US011756658B2

United States Patent
Wang

(10) Patent No.: US 11,756,658 B2
(45) Date of Patent: Sep. 12, 2023

(54) MEDICAL INFORMATION QUERY SYSTEM AND METHOD

(71) Applicant: BOE TECHNOLOGY GROUP CO., LTD, Beijing (CN)

(72) Inventor: Lvwei Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 197 days.

(21) Appl. No.: 16/327,992

(22) PCT Filed: May 16, 2018

(86) PCT No.: PCT/CN2018/087081
§ 371 (c)(1),
(2) Date: Feb. 25, 2019

(87) PCT Pub. No.: WO2018/223823
PCT Pub. Date: Dec. 13, 2018

(65) Prior Publication Data
US 2019/0228849 A1    Jul. 25, 2019

(30) Foreign Application Priority Data

Jun. 9, 2017 (CN) .......................... 201710433143.5

(51) Int. Cl.
*G16H 10/60* (2018.01)
*G16H 50/30* (2018.01)
*G16H 10/40* (2018.01)
*G16H 50/20* (2018.01)
(Continued)

(52) U.S. Cl.
CPC ............ *G16H 10/60* (2018.01); *G06F 16/50* (2019.01); *G16H 10/40* (2018.01); *G16H 20/40* (2018.01);
(Continued)

(58) Field of Classification Search
CPC ........ G16H 10/60; G16H 20/40; G16H 50/50; G16H 50/30; G16H 50/20; G16H 20/60;
(Continued)

(56) References Cited

U.S. PATENT DOCUMENTS

2011/0077973 A1* 3/2011 Breitenstein ........... G06Q 10/10
705/3
2014/0172914 A1* 6/2014 Elnikety ............. G06F 16/9024
707/774
(Continued)

FOREIGN PATENT DOCUMENTS

CN         102043812 A      5/2011
CN         102163218 A      8/2011
(Continued)

OTHER PUBLICATIONS

Combi et al., Conceptual Modeling of Temporal Clinical Workflows, 14th International Symposium on Temporal Representation and Reasoning (Year: 2007).*
(Continued)

*Primary Examiner* — Evangeline Barr
*Assistant Examiner* — Jordan L Jackson
(74) *Attorney, Agent, or Firm* — Dilworth & Barrese. LLP.; Michael J. Musella, Esq.

(57) ABSTRACT

A medical information query system is provided. The medical information query system includes: a processor and a memory, wherein the memory is configured to store computer instructions: and the processor is configured to load the computer instructions and execute: receiving clinical data and acquiring query rules matched with the clinical data; and inquiring medical information corresponding to the query rules in a graphic database.

5 Claims, 5 Drawing Sheets

(51) Int. Cl.
  *G06F 16/50* (2019.01)
  *G16H 20/60* (2018.01)
  *G16H 50/50* (2018.01)
  *G16H 20/40* (2018.01)
  *G06F 16/53* (2019.01)
  *G16H 20/10* (2018.01)
  *G16H 20/30* (2018.01)

(52) U.S. Cl.
  CPC ............. *G16H 20/60* (2018.01); *G16H 50/20* (2018.01); *G16H 50/30* (2018.01); *G16H 50/50* (2018.01); *G06F 16/53* (2019.01); *G16H 20/10* (2018.01); *G16H 20/30* (2018.01)

(58) Field of Classification Search
  CPC ........ G16H 20/30; G16H 20/10; G16H 10/40; G06F 16/53; G06F 16/50
  See application file for complete search history.

(56) References Cited

U.S. PATENT DOCUMENTS

| | | | | |
|---|---|---|---|---|
| 2015/0254370 | A1* | 9/2015 | Sexton | G06F 19/00 707/798 |
| 2016/0063212 | A1* | 3/2016 | Monier | G16H 50/50 705/3 |
| 2016/0328443 | A1* | 11/2016 | Abraham | G06F 16/24524 |
| 2016/0364532 | A1 | 12/2016 | Honeycutt et al. | |
| 2017/0277841 | A1* | 9/2017 | Shankar | G16Z 99/00 |
| 2018/0108443 | A1* | 4/2018 | Li | G16H 50/20 |
| 2018/0365337 | A1* | 12/2018 | Sexton | G06F 16/26 |
| 2019/0228849 | A1 | 7/2019 | Wang | |

FOREIGN PATENT DOCUMENTS

| | | |
|---|---|---|
| CN | 103177108 A | 6/2013 |
| CN | 106021281 A | 10/2016 |
| CN | 107239665 A | 10/2017 |

OTHER PUBLICATIONS

Roy et al, Using Word Embeddings for Automatic Query Expansion, Neu-IR '16 SIGIR Workshop on Neural Information Retrieval (Jul. 16, 2016) (Year: 2016).*

Sondhi and Sun, SympGraph: A framework for mining clinical notes through symptom relation graphs, KDD '12: Proceedings of the 18th ACM SIGKDD international conference on Knowledge discovery and data mining (Aug. 2012) (Year: 2012).*

Lysenko et al., Representing and querying disease networks using graph databases, 9(23) Biodata Mining 1-19 (Year: 2016).*

Yuan Ling, Methods and Techniques for Clinical Text Modeling and Analytics, PhD Dissertation—Drexel University (Feb. 2017) (Year: 2017).*

Röhrig et al., Directed acyclic graphs helped to identify confounding in the association of disability and electrocardiographic findings : results from the KORA-Age study, 67 J of Clinical Epidemiology 199-206 (Year: 2014).*

Kamsu Foguem et al., Using conceptual graphs for clinical guidelines representation and knowledge visualization, 16(4) Information Systems Frontiers 571-589 (Year: 2014).*

International Search Report and Written Opinion dated Aug. 13, 2018 from State Intellectual Property Office of the P.R. China.

Second Chinese Office Action dated Oct. 9, 2019.

* cited by examiner

MEDICAL INFORMATION QUERY SYSTEM AND METHOD

CROSS REFERENCE TO RELATED APPLICATION

The present application claims the priority of Chinese patent application No. 201710433143.5, filed on Jun. 9, 2017, and the entire content disclosed by the Chinese patent application is incorporated herein by reference as part of the present application.

TECHNICAL FIELD

Embodiments of the present disclosure relate to a medical information query system and a medical information query method.

BACKGROUND

Decision support system (DSS) is defined as "a computer application system that assists a manager in a decision-making process for semi-structured problems, supports rather than replaces the manager to make judgments, and improves the effectiveness of decisions rather than efficiency".

SUMMARY

At least one embodiment of the present disclosure provides a medical information query system, comprising: a processor and a memory. The memory is configured to store computer instructions; and the processor is configured to load the instructions and execute: receiving clinical data and acquiring query rules matched with the clinical data; and inquiring medical information corresponding to the query rules in a graphic database.

For example, receiving the clinical data and acquiring the query rules matched with the clinical data comprises: acquiring a first clinical factor and a first clinical relationship which are matched with the clinical data according to selected rules.

For example, the first clinical factor comprises at least one of the group consisting of: disease type, drug type, treatment mode, health education, experimental data and symptom.

For example, the first clinical relationship comprises at least one of the group consisting of: risk relationship, taboo relationship, affiliation relationship, treatment relationship and attention relationship.

For example, the graphic database comprises a plurality of nodes and directed line segments connected between the nodes, the nodes represent a plurality of clinical factors, and the directed line segments represent clinical relationships between the clinical factors.

For example, the clinical factors comprise at least one of the group consisting of: disease type, drug type, treatment mode, health education, experimental data and symptom.

For example, the clinical relationships comprise at least one of the group consisting of: risk relationship, taboo relationship, affiliation relationship, treatment relationship and attention relationship.

For example, inquiring the medical information corresponding to the query rules in the graphic database comprises: acquiring a first node corresponding to the first clinical factor; acquiring a first directed line segment satisfying the first clinical relationship out of directed line segments relevant to the first node; acquiring a second node which is directed to by the first directed line segment; and acquiring the medical information corresponding to the query rules according to the clinical factor represented by the second node.

For example, the processor is configured to load the instructions and execute: receiving original clinical data before receiving the clinical data; and obtaining the clinical data by preprocessing the original clinical data, which is received, according to preprocessing rules.

For example, the processor is configured to load the instructions and execute: pushing the inquired medical information corresponding to the query rules to a user after inquiring the medical information corresponding to the query rules in the graphic database.

At least one embodiment of the present disclosure provides a medical information query method, comprising: receiving clinical data; acquiring query rules matched with the clinical data; and inquiring medical information corresponding to the query rules in a graphic database.

For example, acquiring the query rules matched with the clinical data comprises: acquiring a first clinical factor and a first clinical relationship which are matched with the clinical data according to selected rules.

For example, the first clinical factor comprises at least one of the group consisting of: disease type, drug type, treatment mode, health education, experimental data and symptom.

For example, the first clinical relationship comprises at least one of the group consisting of: risk relationship, taboo relationship, affiliation relationship, treatment relationship and attention relationship.

For example, the graphic database comprises a plurality of nodes and directed line segments connected between the nodes, the nodes represent a plurality of clinical factors, and the directed line segments represent clinical relationships between the clinical factors.

For example, the clinical factors comprise at least one of the group consisting of: disease type, drug type, treatment mode, health education, experimental data and symptom.

For example, the clinical relationships comprise at least one of the group consisting of: risk relationship, taboo relationship, affiliation relationship, treatment relationship and attention relationship.

For example, inquiring the medical information corresponding to the query rules in the graphic database comprises: acquiring a first node corresponding to the first clinical factor; acquiring a first directed line segment satisfying the first clinical relationship out of directed line segments relevant to the first node; acquiring a second node which is directed to by the first directed line segment; and acquiring the medical information corresponding to the query rules according to the clinical factor represented by the second node.

For example, before receiving the clinical data, the method further comprises: receiving original clinical data; and obtaining the clinical data by preprocessing the original clinical data, which is received, according to preprocessing rules.

For example, after inquiring the medical information corresponding to the query rules in the graphic database, the method further comprises: pushing the medical information corresponding to the query rules to a user.

BRIEF DESCRIPTION OF THE DRAWINGS

In order to demonstrate clearly technical solutions of the embodiments of the present disclosure, the accompanying drawings in relevant embodiments of the present disclosure will be introduced briefly. It is apparent that the drawings may only relate to some embodiments of the disclosure. Other drawings may also be obtained from those of ordinary skill in the art based on these drawings without the inventive labor.

DETAILED DESCRIPTION

The technical solutions of the embodiments will be described in a clearly and fully understandable way in connection with the drawings related to the embodiments of the disclosure. It is apparent that the described embodiments are just a part but not all of the embodiments of the disclosure. Based on the described embodiments herein, those skilled in the art can obtain other embodiment, without any creative work, which shall be within the scope of the disclosure.

It is known by the inventors of the present application that a decision support system (DSS) is generally defined as a computer application system that assists a decision maker to make a semi-structured or unstructured decision via human-computer interaction through data, models, and knowledge. With a development of artificial intelligence technology and information processing technology, DSS has been widely used in the industry and has solved a series of representative decision support problems. For example, a clinical decision support system (CDSS) is a system that specifically assists in clinical diagnosis. At the time of the doctor's consultation, the CDSS uses the existing expert knowledge base, clinical practice guidelines, case analysis and other data to analyze a patient's symptoms and give medical advice, so that a user can conveniently inquire corresponding medical advice and medical knowledge. The CDSS can effectively solve the limitation problem of clinician knowledge, reduce human negligence, and relatively reduce medical expenses.

In the above-mentioned system for medical advice and medical knowledge query based on clinical data, a rule engine module uses a relational database to store diagnostic decisions, making the query complex, slow, and unexpected, and as the rule engine module stores a database and is coupled with an underlying database, the complexity of development and maintenance can be high.

Figure 1:
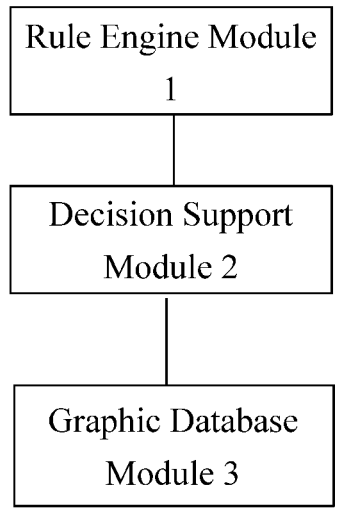
FIG. 1 and FIG. 1a are respectively a structural block diagram of a medical information query system provided by some embodiments of the present disclosure.

Some embodiments of the present disclosure disclose a medical information query system. The medical information query system can be connected with an external device through various kinds of programmatic interfaces, such as a Java interface. As shown in FIG. 1, the medical information query system can logically include: a rule engine module 1, a decision support module 2 and a graphic database module 3. The medical information query system can be implemented by executing computer programs or the like through a computer product (a local server or cloud computing), and can also be implemented by a special-purpose logic operation processing device with related computer instructions.

Figure 1A:
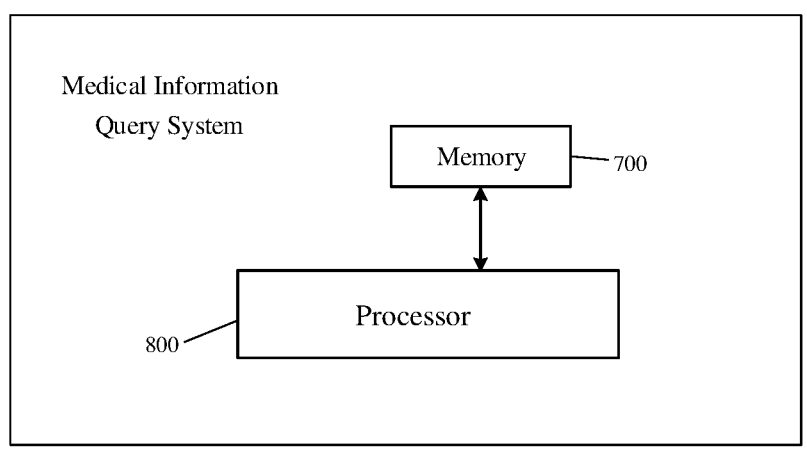

As shown in FIG. 1a, the medical information query system includes a memory 700 and a processor 800. The memory 700 is configured to store computer program instructions. The processor 800 is configured to execute the work flows of the rule engine module 1, the decision support module 2 and the graphic database module 3 and realize the functions of the rule engine module 1, the decision support module 2 and the graphic database module 3 when loading the program instructions in the memory 700.

For example, the rule engine module 1 is configured to receive clinical data and acquire query rules matched with the clinical data.

For example, the clinical data can be a patient's basic signs, test results, etc. The query rules can reflect the clinical data and processing modes of corresponding clinical data.

In some embodiments, the rule engine module 1 adopts an application framework that receives data input, interprets business rules, and makes business decisions based on the business rules. For example, the rule engine module 1 adopts a Drools framework. As a core framework of the system, the Drools framework has the advantages of easy to adjust rules, manage, integrate, and extend query rules. Therefore, the framework has good compatibility with other systems, can use XML files to edit and store rules, and further ensures that the rules can be easily modified, adjusted and managed.

For example, the graphic database module 3 is configured to store a graphic database. The graphic database is used for recording medical information. The medical information can be diagnosis and treatment advice, medical knowledge, etc. The medical information is a massive amount of information. The medical information can be provided by professional literature and medical experts. These professional advice of the professional literature and the medical experts have scientificalness and normalization and become reliable knowledge sources. For example, the professional literature may be Guide to Clinical Practice, which is taken as a guiding document issued by an authoritative medical institution to help clinicians and patients to make appropriate treatment and has been widely recognized by the medical community.

In some embodiments, in a case where the medical information is generally a vast amount of unstructured text information, in order for the medical information to be read and executed quickly and efficiently by the system, it is necessary to convert the text information into structured medical knowledge. Therefore, a clinical pathway can be pre-established for the medical information. The clinical pathway is a method for establishing a standardized treatment model and treatment procedure for a certain disease and promoting tissue treatment and disease management with the guidance of evidence-based medical evidence and manual, which ultimately has a function of regulating medical behavior, reducing variation, reducing costs, and improving quality. Further, the clinical pathway in the embodiment of the present disclosure also includes a system formed by relevant medical knowledge. In order to apply the clinical pathway to the medical information query system provided by the embodiment, the graphic database is adopted to store the medical information in which the clinical pathway is established.

In some embodiments, the graphic database stored by the graphic database module 3 can be a Neo4j graphic database. The Neo4j graphic database uses Cypher language for query work, and the Cypher language is a query language similar to SQL. The adoption of the graphic database to store the medical information also makes the query more convenient.

For example, the decision support module 2 is configured to inquire medical information, corresponding to the query rules acquired by the rule engine module 1, in the graphic database stored by the graphic database module 3.

Therefore, by adoption of the above-mentioned structural design, the rule engine module 1 is only configured to acquire the query rules matched with the clinical data, only transmits the query rules to the decision support module 2, and does not store the medical information, and the graphic database 3 stores the medical information. Thus, the load of the rule engine module 1 can be reduced, so that the rule engine module 1 can quickly respond to the mission requirement of the decision support module 2, and the efficiency of the rule engine module 1 can be high. In addition, the rule engine module 1 and the graphic database module 3 respectively exchange information with the decision support module 2, and the rule engine module 1 and the graphic database module 3 do not exchange information with each other. The rule engine module 1 and the graphic database module 3 are independent of each other, and do not directly transmit data. Therefore, the rule engine module 1 is not coupled with the graphic database module 3, thereby simplifying the development and maintenance complexity of the system and saving the storage space and the query time.

Figure 2:
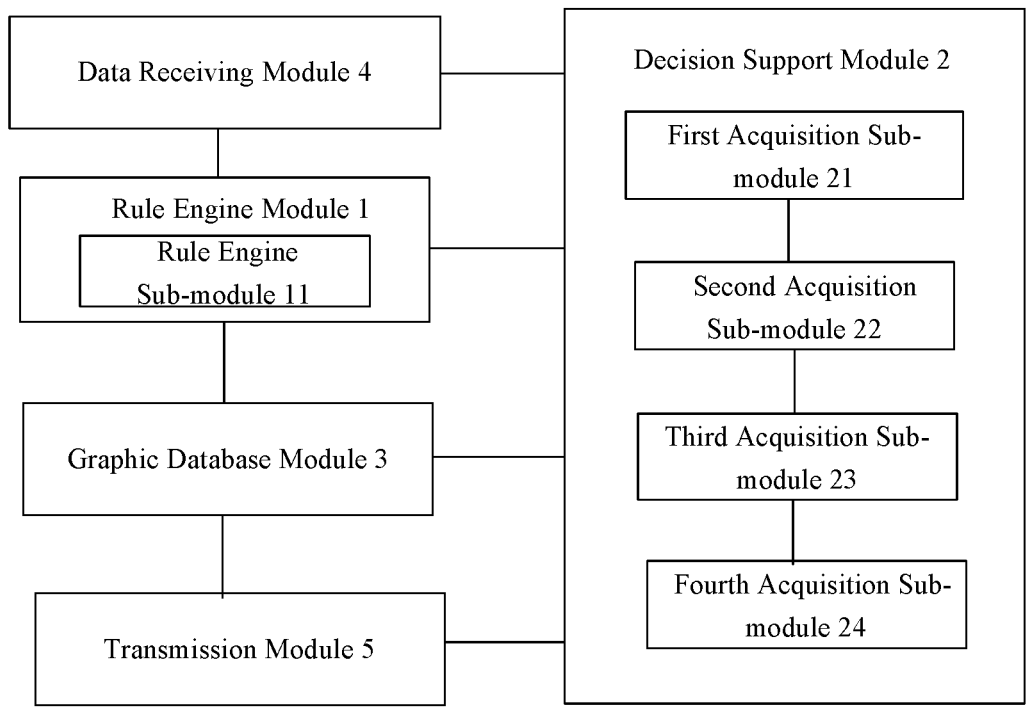
FIG. 2 is another structural block diagram of a medical information query system provided by some embodiments of the present disclosure.

According to some examples of the present disclosure, as shown in FIG. 2, the rule engine module 1 includes a rule engine sub-module 11.

The rule engine sub-module 11 is configured to acquire a first clinical factor and a first clinical relationship which are matched with the clinical data according to selected rules.

The first clinical factor and the first clinical relationship are the query rules. The selected rules are general systematic rules determined according to the clinical pathway. After receiving the clinical data, the rule engine sub-module 11 can acquire the query rules, namely the first clinical factor and the first clinical relationship which are matched with the clinical data, after the determination of rules layer by layer.

For example, the first clinical factor includes at least one of the group consisting of: disease type, drug type, treatment mode, health education, experimental data and symptom.

For example, the disease types may include heart disease, diabetes, gallstones, etc. The drug types may include hypotensor, antiphlogistic drug, pain-killer, etc. The treatment modes may include exercise therapy, medication, surgical treatment, etc. The health education may include eating habit, scientific exercise, disease prevention, etc. The experimental data may include fasting blood glucose, hemoglobin value, platelet count, etc. The symptoms may include stomachache, edema, blister, etc.

It should be understood that the first clinical factor is not limited to the types listed above, and the first clinical factor of other types can be added as required.

The first clinical relationship includes at least one of the group consisting of: risk relationship, taboo relationship, affiliation relationship, treatment relationship and attention relationship.

The risk relationship means that if A occurs, it may lead to the occurrence of B indicated by the risk relationship. For example, A refers to that: 2 hours after a meal, blood glucose is higher than 7.0 mmol/L; and B indicated by the risk relationship refers to: diabetes, indicating that if the blood glucose is higher than 7.0 mmol/L2 hours after the meal, there is a risk of diabetes.

The taboo relationship means that if A occurs, B corresponding to the taboo relationship should be prohibited. For example, A is threatened abortion; and B indicated by the taboo relationship is exercise therapy, indicating that when there are signs of threatened abortion, exercise therapy shall not be adopted for treatment.

The affiliation relationship means that if A occurs, B indicated by the affiliation relationship belongs to A, or B indicated by the affiliation relationship includes A. For example, A is exercise therapy; and B indicated by the affiliation relationship is aerobic exercise, indicating that exercise therapy includes aerobic exercise.

The treatment relationship means that if A occurs, B indicated by the treatment relationship can be used to treat A. For example, A is diabetes; and B indicated by the treatment relationship is hypoglycemic drug, indicating that after getting diabetes, hypoglycemic drug can be taken for treatment.

Attention relationship means that if A occurs, B indicated by the attention relationship should be paid attention. For example, this attention may be based on A, prompting for subsequent possible symptoms; or this attention may be based on A, prompting for subsequent physical examination; or this attention may be based on A, suggesting the habit to be maintained. For example, A is diabetes; and B indicated by the attention relationship refers to: timed quantitative eating, indicating that after getting diabetes, it is necessary to pay attention to timed quantitative eating.

It should be understood that the first clinical relationship is not limited to the relationships listed above, and the first clinical relationship of other types can also be added as required.

Figure 3:
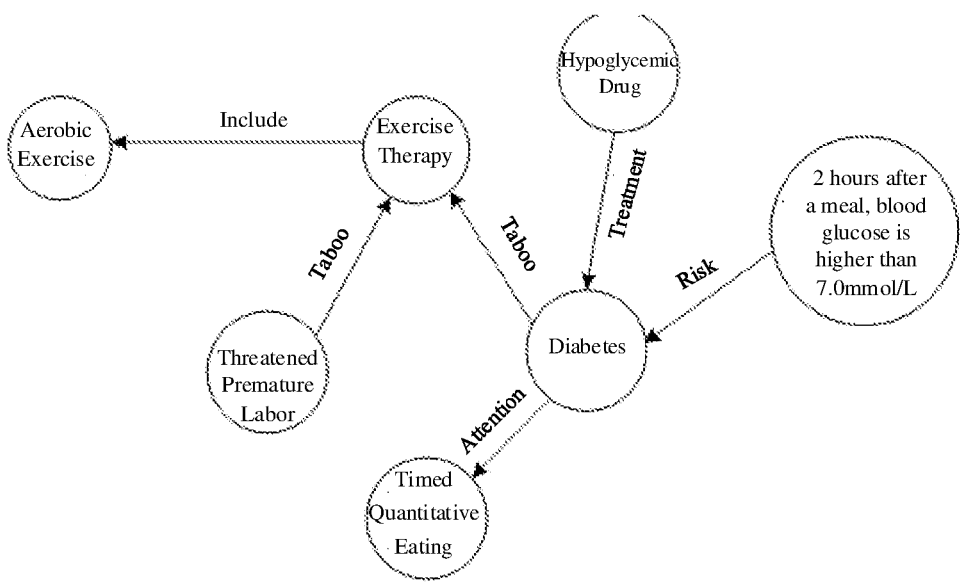
FIG. 3 is a schematic structural diagram of a graphic database in some embodiments of the present disclosure.

Therefore, based on the first clinical factor and the first clinical relationship, the graphic database stored by the graphic database module 3 includes a plurality of nodes and directed line segments connected between the nodes. The nodes represent a plurality of clinical factors. Similarly, the clinical factors include at least one of the group consisting of: disease type, drug type, treatment mode, health education, experimental data and symptom, which may specifically refer to the first clinical factor, and details are not described here again. The directed line segments represent clinical relationships between the clinical factors. Similarly, the clinical relationships include at least one of the group consisting of: risk relationship, taboo relationship, affiliation relationship, treatment relationship and attention relationship, which may specifically refer to the first clinical relationship, and details are not described here again. The directed line segment may be a unidirectional arrow line segment or a bidirectional arrow line segment. In two nodes connected by a arrow line segment, the clinical factor indicated by the node oriented by the arrow is the result obtained from the clinical factor indicated by another connected node according to the clinical relationship indicated by the directed line segment. FIG. 3 is a schematic structural diagram of a graphic database.

According to some examples of the present disclosure, as shown in FIG. 2, the decision support module 2 includes a first acquisition sub-module 21, a second acquisition sub-module 22, a third acquisition sub-module 23 and a fourth acquisition sub-module 24.

The first acquisition sub-module 21 is configured to acquire a first node corresponding to the first clinical factor.

The first node is a node in the graphic database. The clinical factor in the graphic database includes the first clinical factor. Therefore, the first clinical factor can be represented by corresponding node in the graphic database. For example, if the first clinical factor is diabetes, one node in the graphic database is diabetes. The first acquisition sub-module 21 can acquire the node as the first node corresponding to the first clinical factor.

The second acquisition sub-module 22 is configured to acquire a first directed line segment satisfying the first clinical relationship out of directed line segments relevant to the first node.

The first node acquired by the first acquisition sub-module 21 may be connected with a plurality of directed line segments in the graphic database. The clinical relationship indicated by each of the directed line segments is different. The second acquisition sub-module 22 can acquire the first directed line segment satisfying the first clinical relationship from these directed line segments according to the first clinical relationship.

The third acquisition sub-module 23 is configured to acquire a second node which is directed to by the first directed line segment.

After the first node and the first directed line segment are acquired, at least one second node can be acquired from the nodes of the graphic database according to the first directed line segment.

The fourth acquisition sub-module 24 is configured to acquire the medical information corresponding to the query rules according to the clinical factor represented by the second node.

The clinical factor represented by the second node is the medical information corresponding to the query rules.

By adoption of the design of the decision support module 2, corresponding node and directed line segment can be inquired in the graphic database stored by the graphic database module 3 according to the first clinical factor and the first clinical relationship, a node which is directed to by the directed line segment can be acquired, and required medical information can be acquired according to the clinical factor represented by the node.

According to some examples of the present disclosure, as shown in FIG. 2, the medical information query system further includes a data receiving module 4.

The data receiving module 4 is configured to receive original clinical data before the rule engine module 1 receiving the clinical data.

The user can input the original clinical data by means of keyboard, touch panel or the like, so the data receiving module 4 can receive the original clinical data.

In some embodiments, the decision support module 2 is configured to obtain clinical data by preprocessing the original clinical data, which is received by the data receiving module 4, according to preprocessing rules.

The format of the inputted original clinical data may be multiple according to the habits of different users. The original clinical data in multiple formats are not convenient for the medical information query system to analyze and process. Therefore, the decision support module 2 preprocesses these original clinical data, and converts these original clinical data into clinical data in standard format according to the preprocessing rules, so the medical information query system performs corresponding analysis and processing on the clinical data.

According to some examples of the present disclosure, as shown in FIG. 2, the medical information query system further includes a transmission module 5.

The transmission module 5 is configured to push the medical information corresponding to the query rules inquired by the decision support module 2 to a user after the decision support module 2 inquiring the medical information corresponding to the query rules in the graphic database stored by the graphic database module 3.

For example, the transmission module 5 can push the medical information to the user by text, voice or the like, so the user can obtain the required medical information.

The medical information query system provided by the embodiment of the present disclosure can reduce the load of the rule engine module 1 by adopting the above structural design, so the rule engine module 1 can rapidly respond to the mission requirement of the decision support module 2, and the efficiency of the rule engine module 1 can be high. In addition, the rule engine module 1 is not coupled with the graphic database module 3, thereby simplifying the development and maintenance complexity of the system and saving the storage space and the query time. In addition, the adoption of the graphic database to store the medical information also makes the query more convenient.

Figure 4:
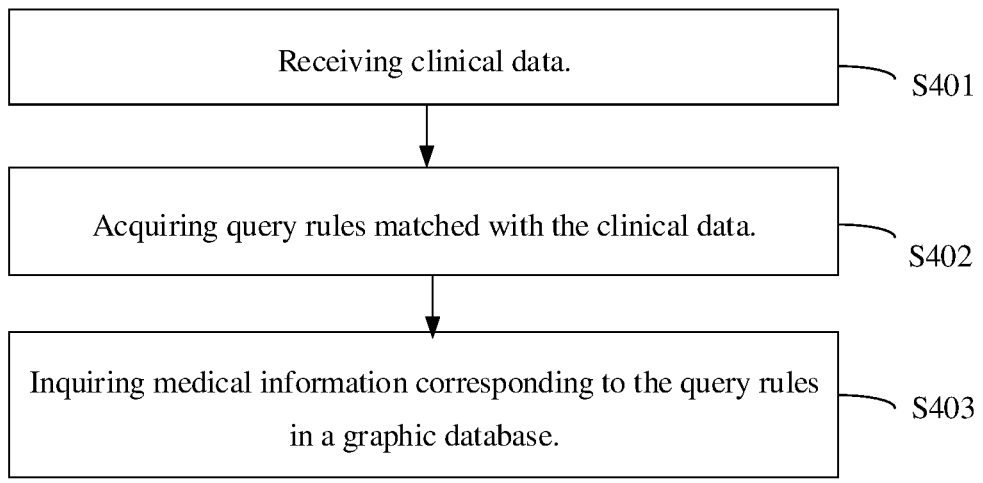
FIG. 4 is a flowchart of a medical information query method provided by some embodiments of the present disclosure.

The embodiment of the present disclosure discloses a medical information query method. As shown in FIG. 4, the method includes the following steps.

S401: receiving clinical data.

For example, the clinical data may be a patient's basic signs, test results, etc.

S402: acquiring query rules matched with the clinical data.

The query rules can reflect the clinical data and processing modes of corresponding clinical data. For example, the clinical data is: 2 hours after a meal, blood glucose is higher than 7.0 mmol/L; and the corresponding processing mode of the clinical data is the matter that should be paid attention to in response to the blood glucose.

S403: inquiring medical information corresponding to the query rules in a graphic database.

The graphic database includes a plurality of nodes and directed line segments connected between the nodes. The nodes represent a plurality of clinical factors. The directed line segments represent clinical relationships between the clinical factors. The clinical factors include at least one of the group consisting of: disease type, drug type, treatment mode, health education, experimental data and symptom, which may specifically refer to the above embodiments, and details are not described here again. The clinical relationships include at least one of the group consisting of: risk relationship, taboo relationship, affiliation relationship, treatment relationship and attention relationship, which may specifically refer to the above embodiments, and details are not described here again.

Therefore, corresponding medical information can be acquired through the graphic database.

According to some examples of the present disclosure, the step S402 specifically includes the following process.

acquiring a first clinical factor and a first clinical relationship which are matched with the clinical data according to selected rules.

The first clinical factor includes at least one of the group consisting of: disease type, drug type, treatment mode, health education, experimental data and symptom, which may specifically refer to the above embodiment, and details are not described here again. The first clinical relationship includes at least one of the group consisting of: risk relationship, taboo relationship, affiliation relationship, treatment relationship and attention relationship, which may specifically refer to the above embodiment, and details are not described here again.

Figure 5:
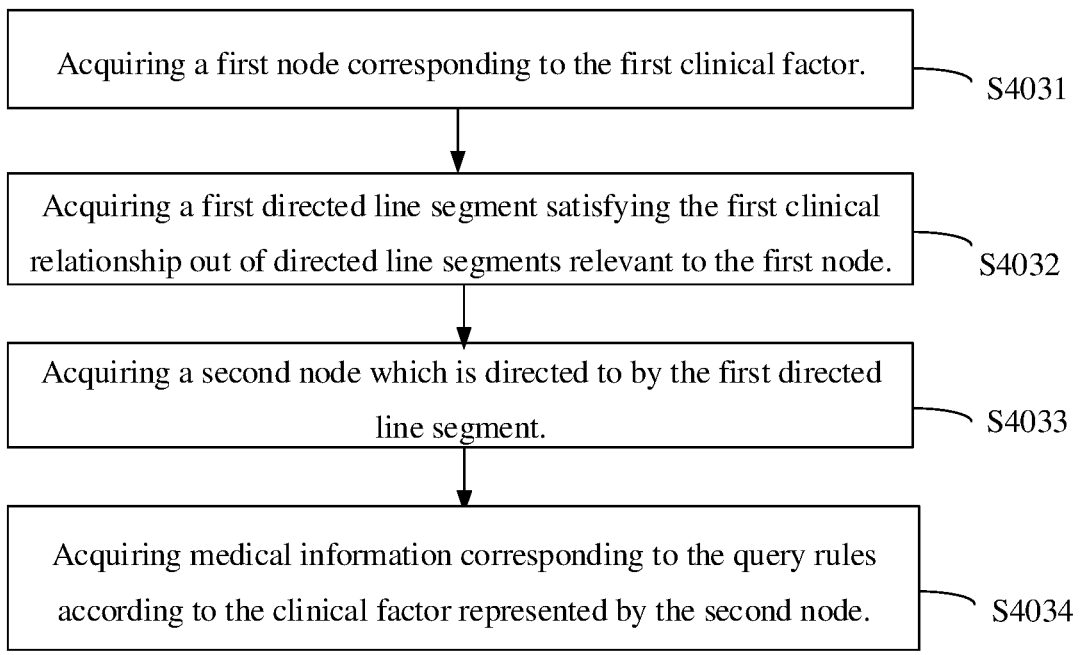
FIG. 5 is a flowchart illustrating the step of inquiring medical information corresponding to the query rules in the graphic database in the medical information query method provided by some embodiments of the present disclosure.

According to some examples of the present disclosure, as shown in FIG. 5, the step S403 includes the following processes.

S4031: acquiring a first node corresponding to the first clinical factor.

The first node is a node in the graphic database. The clinical factor in the graphic database includes the first clinical factor. Therefore, the first clinical factor can be represented by corresponding node in the graphic database.

S4032: acquiring a first directed line segment satisfying the first clinical relationship out of directed line segments relevant to the first node.

The first node acquired in the step S4031 may be connected with a plurality of directed line segments in the graphic database. The clinical relationship indicated by each of the directed line segments is different. According to the first clinical relationship, the first directed line segment satisfying the first clinical relationship can be acquired from these directed line segments through the step 4032.

S4033: acquiring a second node which is directed to by the first directed line segment.

After the first node and the first directed line segment are acquired, at least one second node can be acquired from the nodes of the graphic database according to the first directed line segment.

S4034: acquiring medical information corresponding to the query rules according to the clinical factor represented by the second node.

The clinical factor represented by the second node is the medical information corresponding to the query rules.

Therefore, after the above steps, corresponding nodes and directed line segments can be inquired in the graphic database according to the first clinical factor and the first clinical relationship; a node which is directed to by the directed line segment can be acquired; and the required medical information is acquired according to the clinical factor represented by the node.

In some embodiments, the clinical data is also preprocessed before the step of receiving the clinical data, so the clinical data can be data in a unified format and can be conveniently analyzed and processed.

In some embodiments, after the step of inquiring the medical information corresponding to the query rules in the graphic database, the medical information is also fed back to a user, so the user can obtain the required medical information.

Figure 6:
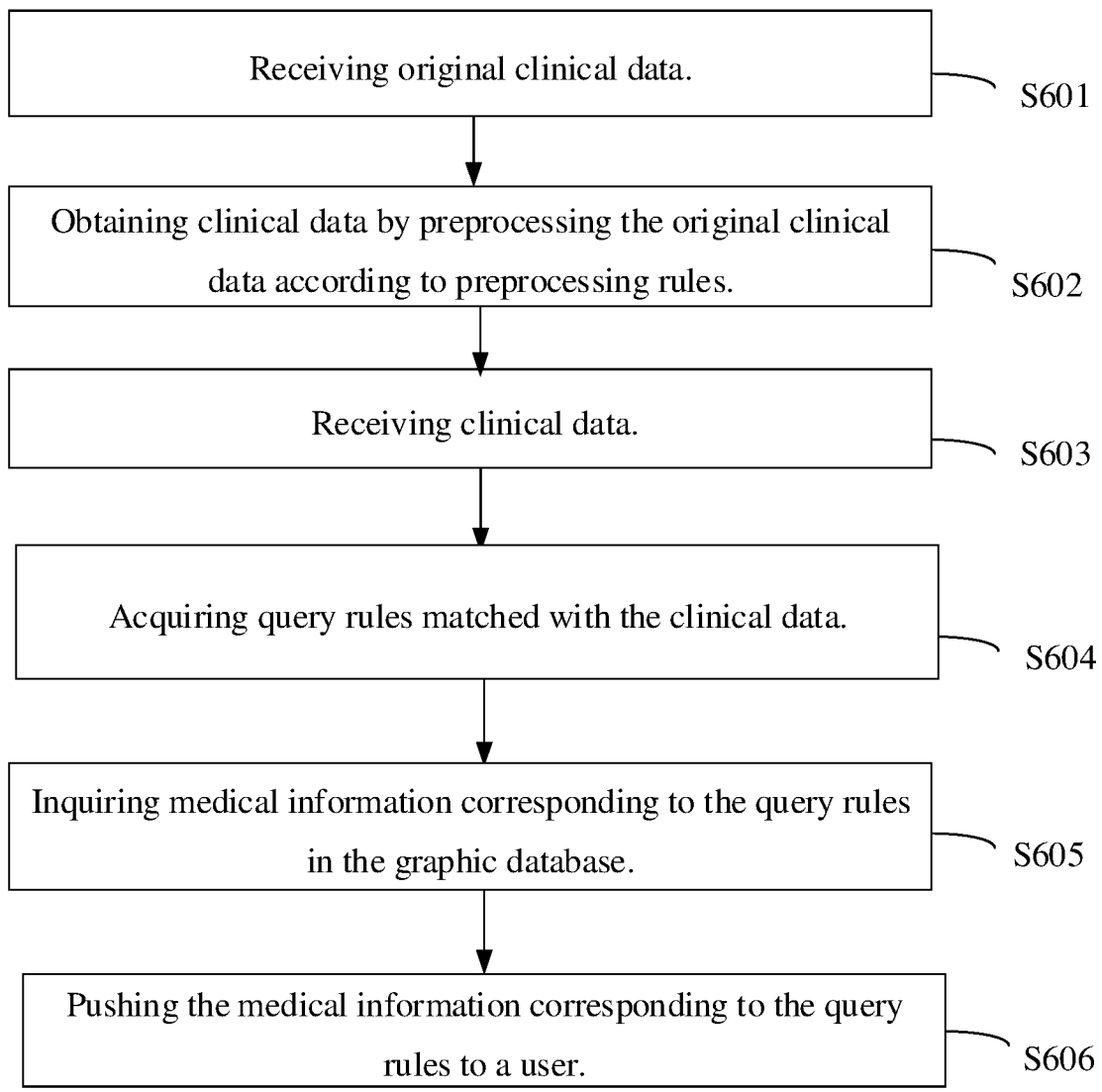
FIG. 6 is another flowchart of a medical information query method provided by some embodiments of the present disclosure.

In some embodiments, as shown in FIG. 6, the method further includes the following steps.

S601: receiving original clinical data.

For example, the user can input the original clinical data by means of keyboard, touch panel, etc.

S602: obtaining the clinical data by preprocessing the original clinical data according to preprocessing rules.

The format of the inputted original clinical data may be multiple according to the habits of different users. The original clinical data in multiple formats are not convenient to analyze. Therefore, these original clinical data are preprocessed in advance, so these original clinical data can be converted into clinical data in standard format according to the preprocessing rules, and then the clinical data can be correspondingly analyzed and processed.

S603: receiving clinical data.

S604: acquiring query rules matched with the clinical data.

S605: inquiring medical information corresponding to the query rules in the graphic database.

The above three steps respectively correspond to the steps S401-S403, and details are not described here again.

S606: pushing the medical information corresponding to the query rules to a user.

For example, the medical information can be push to the user by means of text, voice or the like, so the user can obtain the required medical information.

In summary, the medical information query method provided by the embodiment of the present disclosure acquires the query rules according to the clinical data, acquires corresponding medical information in the graphic database according to the query rules, makes the query more convenient, and has a higher efficiency.

Figure 7:
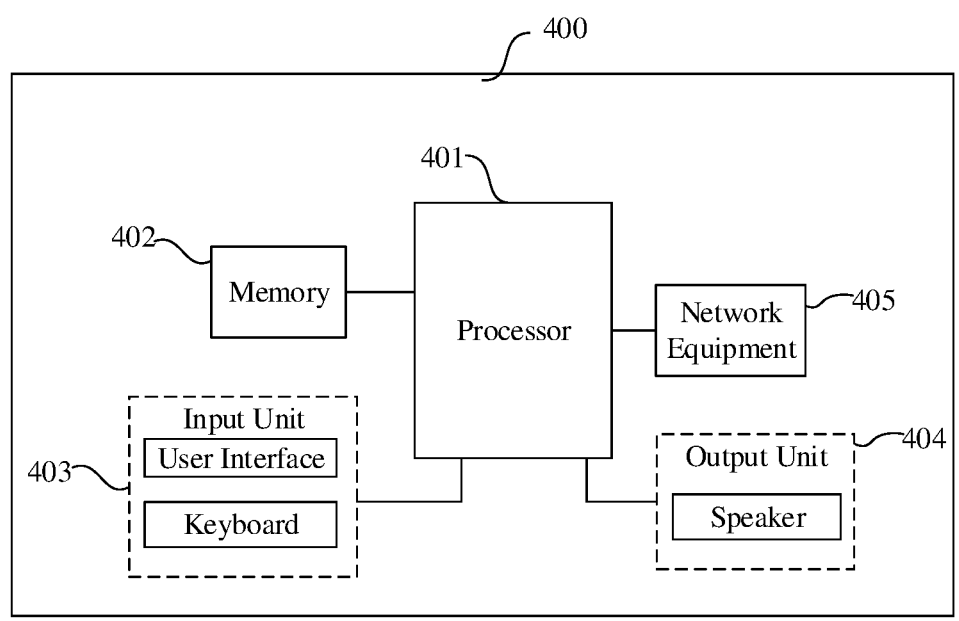
FIG. 7 is a schematic structural diagram of a computer product in the embodiment of the present disclosure.

As shown in FIG. 7, the embodiment of the present disclosure provides a computer product 400, and the computer product 400 includes one or more processors 401. The processor is configured to run computer instructions and execute one or more steps in the medical information query method provided by the embodiments.

Optionally, the computer product 400 further includes a memory 402 which is connected with the processor 401 and configured to store the computer instructions.

The computer product 400 can be implemented as a local computing computer product structure, namely the medical information query method provided by the above embodiment is implemented on a user side computer; and can also be implemented as a local and remote interactive computer product structure, namely partial steps in the medical information query method provided by the above embodiment are implemented on the user side terminal, and other steps in the medical information query method provided by the above embodiment are implemented on a network terminal connected with the user side terminal.

The processor 401 can be a central processing unit (CPU), a field programmable logic array (FPGA), a microcontroller unit (MCU), a digital signal processor (DSP), an application-specific integrated circuit (ASIC) or other logic operation devices having data processing capability and/or program execution capability.

The memory 402 can be implemented by any kind of volatile or nonvolatile memory or a combination thereof, e.g., a static random access memory (SRAM), an electrically erasable programmable read only memory (EEPROM), an erasable programmable read-only memory (EPROM), a programmable read-only memory (PROM), a read-only memory (ROM), a magnetic memory, a flash memory, a magnetic disk or a optical disc (CD).

The computer instructions include one or more processor operations defined by an instruction set architecture (ISA) corresponding to the processor. These computer instructions can be logically included in one or more computer programs and represented by the modules in the above embodiments of the present disclosure.

The computer product 400 can also be connected with various kinds of input units 403 (e.g., a user interface, a keyboard, etc.), various kinds of output units 404 (e.g., a speaker, a display, etc.), a network equipment 405 (e.g., a wired network card, a wireless network card, a Bluetooth module, etc.) or the like to realize the interaction between the computer product and other products or users, and details are not described here again.

The network equipment 405 is used for realizing a connection between the computer product 400 and other products or users by, for example, a wireless network, a wired network, and/or any combination of the wireless network and the wired network. The network may include the local area network (LAN), the Internet, the telecommunication network, the Internet of Things based on the Internet and/or the telecommunication network, and/or any combination of the above networks. The wired network, for example, can communicate by means of twisted pair, coaxial cable or optical fiber transmission. The wireless network, for example, can communicate by means of 3G/4G/5G mobile communication network, Bluetooth, Zigbee, Wi-Fi, etc.

The embodiments in the description are described in a progressive manner. Each embodiment focuses on differences from other embodiments. The same or similar parts between the embodiments can refer to each other.

While the preferred embodiments of the present disclosure have been described, those skilled in the art can make further changes and modifications on the embodiments once they know the basic creative concept. Therefore, the appended claims are intended to be interpreted as including the preferred embodiments and all the modifications and variations falling within the scope of the embodiments of the present disclosure.

It should be also finally noted that in the present disclosure, relational terms such as first and second are used merely to distinguish one entity or operation from another entity or operation, and do not necessarily require or imply there is any such actual relationship or order between these entities or operations. Moreover, the term "comprise", "include" or any other variant is intended to cover non-exclusive inclusions, so a process, a method, an article or a terminal device including a series of elements not only includes those elements but also includes other elements not explicitly listed, or also includes elements inherent to such process, method, article or terminal device. Without further limitation, an element defined by the statement "comprising a . . . " does not exclude the existence of additional identical elements in the process, the method, the article or the terminal device including the element.

The foregoing is only the specific embodiments of the present disclosure, but the protection scope of the present disclosure is not limited thereto. Any change or replacement that can be easily thought of by those skilled in the art within the technical scope of the present disclosure shall fall within the protection scope of the present disclosure. Therefore, the protection scope of the present disclosure should be defined by the protection scope of the appended claims.

What is claimed is:

1. A medical information query system, comprising: a processor and a memory, wherein the memory is configured to store computer instructions; and the processor is configured to load the instructions and execute the electrical operations of a rule engine module, a decision support module and a graphic database module, the medical information query system is configured to:
   receiving, by the rule engine module, clinical data and acquiring query rules matched with the clinical data according to systematic rules determined by a clinical pathway, wherein the query rules comprise a first clinical factor and a first clinical relationship which are matched with the clinical data, wherein the clinical pathway is structured medical knowledge extracted from unstructured medical data;
   acquiring, by the decision support module, the query rules from the rule engine module;
   reading, by the decision support module, based on the query rules, a first node corresponding to the first clinical factor in a graphic database stored in the graphic database module, reading a first directed line segment satisfying the first clinical relationship out of directed line segments relevant to the first node, reading a second node which is directed to by the first directed line segment, and reading medical information corresponding to the query rules according to a clinical factor represented by the second node; and
   displaying, on a display terminal, the medical information corresponding to the query rules read in the graphic database to a user,
   wherein the rule engine module is coupled with the decision support module, the graphic database module is coupled with the decision support module, and the rule engine module is decoupled from the graphic database module;
   wherein the graphic database stores unstructured medical data, the unstructured medical data comprises a plurality of nodes and directed line segments connected between the nodes which are established according to the systematic rules determined by the clinical pathway, the nodes represent a plurality of clinical factors, and the directed line segments represent clinical relationships between the clinical factors;
   the clinical factors comprise disease type, drug type, treatment mode, health education, experimental data and symptom; and
   the clinical relationships comprise risk relationship, taboo relationship, affiliation relationship, treatment relationship and attention relationship.

2. The system according to claim 1, wherein the processor is configured to load the instructions and execute:
   receiving original clinical data before receiving the clinical data; and
   obtaining the clinical data by preprocessing the original clinical data, which is received, according to preprocessing rules.

3. A medical information query method, which is executed by a rule engine module, a decision support module and a graphic database module, the method comprising:
   receiving clinical data and acquiring query rules matched with the clinical data, by the rule engine module, according to systematic rules determined by a clinical pathway, wherein the query rules comprise a first clinical factor and a first clinical relationship which are matched with the clinical data, wherein the clinical pathway is structured medical knowledge extracted from unstructured medical data;
   acquiring, by the decision support module, the query rules from the rule engine module;
   reading, by the decision support module, based on the query rules, a first node corresponding to the first clinical factor in a graphic database stored in the graphic database module, reading a first directed line segment satisfying the first clinical relationship out of directed line segments relevant to the first node, reading a second node which is directed to by the first directed line segment, and reading medical information corresponding to the query rules according to a clinical factor represented by the second node; and
   displaying, on a display terminal, the medical information corresponding to the query rules read in the graphic database to a user,
   wherein the rule engine module is coupled with the decision support module, the graphic database module is coupled with the decision support module, and the rule engine module is decoupled from the graphic database module;

wherein the graphic database stores unstructured medical data, the unstructured medical data comprises a plurality of nodes and directed line segments connected between the nodes which are established according to the systematic rules determined by the clinical pathway, the nodes represent a plurality of clinical factors, and the directed line segments represent clinical relationships between the clinical factors;

the clinical factors comprise disease type, drug type, treatment mode, health education, experimental data and symptom; and the clinical relationships comprise risk relationship, taboo relationship, affiliation relationship, treatment relationship and attention relationship.

4. The method according to claim 3, wherein before receiving the clinical data, the method further comprises:

receiving original clinical data; and obtaining the clinical data by preprocessing the original clinical data, which is received, according to preprocessing rules.

5. A medical information query method, which is executed by a medical information query system as claim 1, the method comprising:

receiving clinical data;

acquiring query rules matched with the clinical data, wherein the query rules comprise disease types and treatment modes matched with the clinical data, wherein the treatment modes comprise exercise therapy and medical treatment;

reading a first node corresponding to a disease type in a graphic database;

reading a first directed line segment satisfying a treatment relationship among directed line segments associated with the first node;

reading a second node which is directed by the first directed line segment, and reading medical information corresponding to the query rules according to a treatment mode indicated by the second node; wherein the graphic database comprises nodes representing the disease types and the treatment modes, and directed line segments representing treatment relationships;

pushing electronically the medical information corresponding to the query rules read in the graphic database to a user.

* * * * *